United States Patent [19]

McCully

[11] 4,255,443
[45] Mar. 10, 1981

[54] HOMOCYSTEINE THIOLACTONE PERCHLORATE AS A TUMOR PROMOTOR

[75] Inventor: Kilmer S. McCully, Boston, Mass.

[73] Assignee: The United States of America as represented by the Department of Health, Education and Welfare, Washington, D.C.

[21] Appl. No.: 94,814

[22] Filed: Nov. 16, 1979

Related U.S. Application Data

[63] Continuation of Ser. No. 734,129, Oct. 20, 1976, abandoned, which is a continuation-in-part of Ser. No. 534,836, Dec. 20, 1974, abandoned.

[51] Int. Cl.³ .............................................. A61K 31/38
[52] U.S. Cl. ...................................... 424/275; 549/63
[58] Field of Search .......................... 424/275; 549/63

[56] References Cited

U.S. PATENT DOCUMENTS 3,068,242  12/1962  Schwarze .................................. 549/6

Primary Examiner—Alan Siegel
Attorney, Agent, or Firm—John S. Roberts, Jr.

[57] ABSTRACT

Homocysteine thiolactone perchlorate is prepared from the corresponding homocysteine thiolactone hydrochloride and optimally about two equivalents of perchloric acid as reactants. A preferred solvent utilized is chloroform-methanol (4:1) solution and a preferred temperature range is 0°–85° C. with the lower limit dependent upon the particular solvent and the upper limit of about 186° C. dependent upon the melting point of the product crystals. The preferred perchloric acid reactant may be replaced with perchlorate salts such as $AgClO_4$ or $KClO_4$. The product perchlorate salt is soluble in organic solvents, whereas other known salts such as the hydrochloride are only water soluble. This property is thought to influence the growth effect of the perchlorate salt in animals, such as rabbits, and to influence the unique effect of the perchlorate salt on the growth of malignant tumors in animals, such as mice.

1 Claim, No Drawings

HOMOCYSTEINE THIOLACTONE PERCHLORATE AS A TUMOR PROMOTOR

This is a continuation of application Ser. No. 734,129, filed Oct. 20, 1976, now abandoned, which is a continuation-in-part of Ser. No. 534,836 filed Dec. 20, 1974 now abandoned, of Kilmer S. McCully.

The present invention relates to a specific compound homocysteine thiolactone perchlorate and a method of making same. Homocysteine is $HSCH_2CH_2CH(NH_2)COOH$ and the thiolactone is shown below. Of the known salts of homocysteine thiolactone, the present perchlorate is deemed unique in that it is soluble in organic solvents, whereas other salts such as the hydrochloride are only water soluble. This is of peculiar interest in the unique biologic effect of the perchlorate which is described below.

The reactant homocysteine thiolactone hydrochloride is taught in DP No. 1,081,466 (1958) and this hydrochloride is also the starting material for the present process. Additionally, British Pat. No. 903,322 and Canadian Pat No. 611,437 relate to the homocysteine thiolactone hydrohalide. British Pat No. 903,322 notes the compound at column 2, first page, and Canadian Pat. No. 611,437 describes the chlorohydride at column 2, line 62. Neither of these patent references describes a process or product for the present perchlorate salt.

The literature prior art is listed below:

Kilmer S. McCully, "Homocysteine Metabolism in Scurvy, Growth and Arteriosclerosis," *Nature*, 231:391–392, June 11, 1971.

Kilmer S. McCully, "Homocysteinemia and Arteriosclerosis," *American Heart Journal*, 83:571–573, April 1972.

Eliot Spindel and Kilmer S. McCully, "Conversion of Methionine to Homocysteine Thiolactone in Liver," *Biochimica et Biophysica Acta*, 343:687–691, 1974.

Kilmer S. McCully and Robert B. Wilson, "Homocysteine Theory of Arteriosclerosis," *Atherosclerosis*, 22:215–227 (1975).

Kilmer S. McCully and Peter Clopath, "Homocysteine Compounds Which Influence the Growth of a Malignant Neoplasm," In Press, *Chemotherapy*, 1976.

The compound homocysteine thiolactone perchlorate is produced by the following reaction:

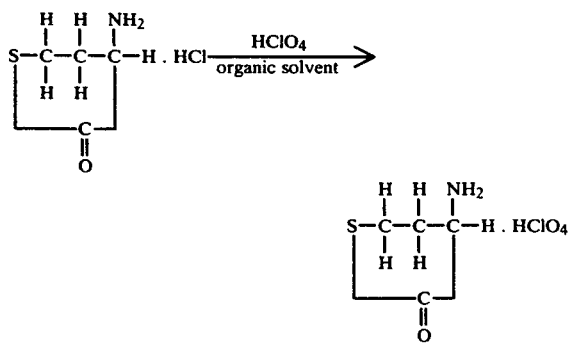

It is surprising to note in the above process, considering that perchloric acid is a powerful oxidizing agent, that the sulfur atom of the starting material is not attacked to produce different oxidized compounds such as homocysteine sulfinic acid instead of the desired present perchlorate salt.

In the above equation the reaction is carried out in organic solvents and a perferred solvent is a mixture of chloroform-methanol (4:1). The temperature parameter of the reaction varies through rather wide limits, ranging from a preferred range of 0°–85° C. to a limiting lower range which would be solvent dependent and a limiting upper range which would be dependent upon the melting point of the crystals produced or about 186° C.

As to the reaction solvent, it is known that the hydrochloride salt and the perchlorate salt of this invention had different water solubilities and that the perchlorate was preferentially soluble in organic solvents. In the present process it has been found that to utilize the different solubilities of the reactant hydrochloride and the product perchlorate, a preferred combination organic solvent could best be utilized. Such a solvent would embody a halogenated hydrocarbon solvent such as chloroform, carbon tetrachloride, or ethylene dichloride as a major component, modified with a minor component of a lower alkanol ($C_1$–$C_6$), such as methanol, ethanol, isopropanol, etc. As less preferred alternatives for the lower alkanol, there may be substituted dioxane, acetonitrile, or aprotic solvents such as dimethyl formamide (DMF) or dimethyl sulfoxide (DMS).

A convenient list of industrial solvents for alcohols and chlorinated hydrocarbons is set out in Kirk-Othmer, *The Encyclopedia of Chemical Technology*, 2d ed., 18:565, 1969, at Table 1.

A particularly apt combination and a preferred one for purposes of this invention is a combination of chloroform and methanol, optimally in a ratio of 4:1 (by volume).

The reaction is favorably affected by an excess of perchloric acid with an optimal stoichiometry of two moles of perchloric acid per mole of hydrochloride salt reactant. The product perchlorate salt is recovered preferably by concentration on a rotary evaporator to crystallize and then recrystallized from chloroform and methanol (4:1 by volume) to produce translucent white crystals with a sharp melting point of 186° C.

The perchlorate salt which is soluble in organic solvents as opposed to other salts, such as the hydrochloride starting material, has growth effects on animals such as mice and rabbits which seem to be dependent upon this solubility property. For example, it has been found that the perchlorate affects the growth of malignant tumors in mice, whereas the hydrochloride is without effect and this indicates that the biological activity of the perchlorate is dependent upon its solubility in non-polar solvents. Thus, the solubility of the perchlorate salt in non-polar solvents makes it uniquely useful in many functions and also screens out any possible use by such salts as the hydrohalide salt.

As to the positive effect of perchlorate in malignant tumors in mice, the following Table I is given where daily doses of homocysteine thiolactone perchlorate (2.5 mg/kg/day) for 10 days showed a sharp increase in the amount of necrosis in the transplanted murine mammary adenocarcinoma. See also Example 3 post.

TABLE 1

| Compound | No. of Tumors | Mean Weight (g ± SEM) | | | | | |
|---|---|---|---|---|---|---|---|
| | | Before Washing | P | After Washing | P | Difference | P |
| — | 7 | 2.383 ± 0.154 | — | 2.111 ± 0.136 | — | .231 ± 0.037 | — |
| HCT . HClO$_4$ | 7 | 2.507 ± 0.100 | >0.1 | 2.197 ± 0.099 | >0.1 | .326 ± 0.029 | .06 |

It has been further found that the homocysteine thiolactone perchlorate was effective in increasing the weight gain of rabbits when fed in a synthetic diet compared to controls. Thus, in the Table 2 below, when compared with similar compounds, it is noted that the weight gain in the perchlorate test was the largest found.

TABLE 2

Weight Gain by Rabbits Fed Homocysteine Derivatives in Synthetic Diet

| Compound Administered | Dose (mg/kg/day) | Weeks on Diet | No. of Rabbits | Mean Weight Gain (g) | P |
|---|---|---|---|---|---|
| — | — | 12 | 6 | 439 ± 59 | — |
| HCT . HClO$_4$ | 110 | 12 | 6 | 892 ± 173 | <0.05 |
| Methionine . HCl | 110 | 12 | 7 | 869 ± 79 | <0.01 |
| Homocystine, oxidized with H$_2$O$_2$ | 40–160 | 12 | 8 | 643 ± 45 | <0.05 |

In the above Table 2, 2–2.5 kg male New Zeland white rabbits were fed a synthetic diet containing homocysteine thiolactone perchlorate (HCT·HClO$_4$), methionine hydrochloride, or oxidized homocystine. One group was fed the synthetic diet without added amino acids. The dose of homocystine, oxidized with H$_2$O$_2$, was 40 mg/kg/day for 4 weeks, 80 for 4 weeks, and 160 for 4 weeks. Mean weight gain ± SEM is given for each group. P-values were calculated for differences from the control group, using the Student t-test.

The unique solubility properties of homocysteine thiolactone perchlorate are also used to advantage in synthesizing novel derivatives of homocysteine thiolactone. For example, N-maleyl homocysteine thiolactone amide and N-(maleamide)-homocysteine thiolactone amide can conveniently be synthesized in toluene, using homocysteine thiolactone perchlorate. Since the analogous homocysteine thiolactone hydrochloride is insoluble in organic solvents required for maleylation, a fusion process must be used which results in racemization to N-fumaryl homocysteine thiolactone amide and a mixture of other products. N-oxalyl homocysteine thiolactone can conveniently be synthesized in tetrahydrofuran from homocysteine thiolactone perchlorate, but the oxalyl derivative cannot be prepared from homocysteine thiolactone hydrochloride because of its insolubility in tetrahydrofuran. These derivatives of homocysteine thiolactone perchlorate may prove to be clinically biologically significant since the two maleyl derivatives both have anti-neoplastic properties when tested in the mouse tumor system described in Example 3. The compounds above suggest that homocysteine thiolactone perchlorate is useful in synthesizing new antineoplastic compounds, some of which are inaccessible if one used as a starting compound homocysteine thiolactone hydrochloride.

It is further known that the present comound homocysteine thiolactone perchlorate is involved in the chain of reactions which occurs when methionine [2-amino-4-(methyl thio)-butanoic acid] is demethylated to homocysteine. It is additionally known that an excess of homocysteine, known as homocysteinemia, is associated with arteriosclerosis. It has been further found that methionine is converted to homocysteine thiolactone in guinea pig liver in vivo within 60 minutes after intraperitoneal injection of [$^{14}$C] methionine. This conversion is the first step of a new pathway by which the sulfur of methionine is transferred to phosphoadenosine phosphosulfate (PAPS). The association of arteriosclerosis with homocysteinemia caused by a deficiency of cystathionine synthetase implies a pathophysiological role for homocysteine derivatives. The arteriosclerotic effect of homocysteine is believed to involve increased sulfation of the proteoglycans in arteriosclerotic plaques. This increased sulfation suggests a transsulfurylation pathway originating from homocysteine (cf. Spindel and McCully, Biochimica et Biophysica Acta, 343:687–691 (1974).

EXAMPLE 1

Preparation of Homocysteine Thiolactone Perchlorate

Homocysteine thiolactone perchlorate was prepared by suspending 30 g homocysteine thiolactone hydrochloride (Nutritional Biochemicals) in 1000 ml chloroform-methanol (4:1, by volume). Two equivalents of 70% HClO$_4$ were added dropwise with stirring until solution was achieved. The solution was concentrated on a rotary evaporator to crystallize the homocysteine thiolactone perchlorate. The crystals were recrystallized to give translucent, white crystals with a sharp melting point at 186° C., light-absorption maximum in water 238 nm (found: C, 22.2; H, 3.3; Cl, 16.4; N, 6.6; O, 36.8; S, 14.9; C$_4$H$_8$ClNO$_5$S requires C, 22.1; H, 3.7; Cl, 16.3; N, 6.4; O, 36.8; S, 14.7%). The crystals yielded a single ninhydrin positive spot, R$_F$0.58, on Mallinckrodt silica gel TLC-TGF plates in chloroform-methanol (4:1, by volume) and a single uniform peak in the position expected for homocysteine thiolactone on the Beckman 120C Amino Acid Analyzer.

EXAMPLE 2

A 400 g fasted guinea pig was injected intraperitoneally with 10 μCi DL-[2-$^{14}$C]methionine (2.5 moles/10 Ci) in 5 ml 5% dextrose. After 1 hour the guinea pig was stunned, and the liver was quickly removed, weighed, and washed twice in normal saline to remove adherent $^{14}$C. The liver was extracted with 20 ml of chloroform-methanol (2:1, by volume) per g tissue, and the extract was washed overnight according to the method of Folche et al, J. Biol. Chem., 191:833–841 (1951). [$^{14}$C]Homocysteine thiolactone was shown to be present in the extract by co-crystallization with excess nonradioactive homocysteine thiolactone perchlorate.

For co-crystallization, 50 ml of the liver extract (about 25,000 cpm) were added to 8 g homocysteine thiolactone perchlorate dissolved in 250 ml chloroform-methanol (4:1, by volume) and stirred at room temperature for 1 hour. The solution was concentrated on a rotary evaporatory to crystallize the homocysteine thiolactone perchlorate. The off-white crystals were recrystallized three more times, decolorizing each time with activated charcoal, to yield large, translucent white crystals with the same sharp melting point and chromatographic mobility as the pure homocysteine thiolactone perchlorate.

After each crystallization, 100-mg samples were counted in 0.5 ml water in 10 ml Aquasol (New England Nuclear). With repeated crystallization, the specific activity of the crystals appraoched a constant value, indicating that [$^{14}$C]homocysteine thiolactone from the liver extract had become incorporated within the crystalline matrix of the synthetic homocysteine thiolactone perchlorate. To exclude any oxidative or ionic effects of the perchlorate, 50 ml of the liver extract (25,000 cpm) were co-crystallized to constant specific activity with 8 g homocysteine thiolactone hydrochloride dissolved in 2000 ml absolute ethanol. To exclude contamination of the [$^{14}$C]methionine with [$^{14}$C]homocysteine thiolactone, 25,000 cpm of [$^{14}$C]methionine were added to 50 ml of non-radioactive liver extract, and co-crystallization with homocysteine thiolactone perchlorate yielded a specific activity which approached the background. When $^{35}$S-labelled homocysteine thiolactone hydrochloride was co-crystallized with homocysteine thiolactone perchlorate, a nearly 100% yield of $^{35}$S was found in the homocysteine thiolactone perchlorate crystals. From these co-crystallization experiments with homocysteine thiolactone perchlorate, homocysteine thiolactone was found to constitute 9.1% of the total $^{14}$C of the chloroform-methanol liver extract as shown in Table 3 below.

TABLE 3

Co-Crystallization of [$^{14}$C] Homocysteine Thiolactone of Lipid Extract

| Carrier | Final spec. act. (cpm/100 mg) | % $^{14}$C in Homocysteine thiolactone |
|---|---|---|
| Homocysteine thiolactone perchlorate | 33 | 9.1 ± .2 |
| Homocysteine thiolactone hydrochloride | 23 | 6.2 |

To show the presence of [$^{14}$C]homocysteine thiolactone in the acid soluble extract of liver, a 400 g fasted guinea pig was injected intraperitoneally with 10 μCi DL-[2-$^{14}$C]- methionine (2 moles/10 Ci) in 10 ml 5% dextrose. After 1 hour, the guinea pig was stunned and the liver was quickly removed, weighed, washed in normal saline, and homogenized in 500 ml buffer (each 500 ml buffer contained 42.5 g sucrose, 4.0 g NaHCO$_3$, 9.5 ml thiodiglycol, and 0.5 g EDTA). The homogenate was decanted and deproteinized three times with excess sulfosalicylic acid. A 5 ml sample of the deproteinized supernatant was chromatographed by the method of Stein and Moore, Cold Spring Harbor Symp. Quant. Biol., 14:179–190 (1949), and the fractions were counted in Bray's solution [Bray, Anal. Biochem., 1:278–285 (1960)]. Using this method, approximately 20% of the acid-soluble $^{14}$C was found in homocysteine thiolactone, as shown in Table 4 below.

TABLE 4

Amino Acid Chromatography of [$^{14}$C] Homocysteine Thiolactone of Acid Extract

| Guinea Pig | % cpm Recovered | % cpm in Homocysteine and Methionine | % cpm in Homocysteine Thiolactone |
|---|---|---|---|
| 1 | 73 | 60 | 19 |
| 2 | 102 | 53 | 20.9 |

These results show that homocysteine thiolactone is a metabolic product of methionine. Therefore, the sulfur of methionine is a source of phosphoadenosine phosphosulfate through the intermediate formation of homocysteine thiolactone, without the prior formation of cystathionine.

The finding of homocysteine thiolactone in the chloroform-methanol and acid extracts of liver demonstated a previously unknown direct dietary source of homocysteine. Thus, homocysteine thiolactone ingested with liver is potentially available for metabolism without prior conversion of free methionine for protein bound methionine to homocysteine thiolactone.

EXAMPLE 3

Homocysteine Thiolactone Perchlorate as Positively Influencing the Growth of a Malignant Neoplasm in Mice The protocol utilized was daily doses of homocysteine thiolactone perchlorate, 2.5 mg/kg/day for 10 days. It was found that the amount of necrosis in the transplanted murine mammary adenocarcinoma increased. 1.5–2.0×10$^7$ A-10 ascites cells were injected subcutaneously in 6 week-old female A/HeJ mice obtained from Jackson Labs, Bar Harbor, Maine. After two weeks the tumors were dissected, weighed, bisected, and reweighed. During the final ten days of tumor growth, homocysteine thiolactone perchlorate, 2.5 mg/kg/day, was injected intraperitoneally. In the chart below are the tumor weights, before and after washing, as well as the difference in weight which is proportional to the amount of necrosis in the tumor.

| Compound | No. of Tumors | Mean Weight (g ± SEM) Before Washing | P | After Washing | P | Difference | P |
|---|---|---|---|---|---|---|---|
| — | 7 | 2.383 ± 0.154 | — | 2.111 ± 0.136 | — | .231 ± 0.037 | — |
| HCT.HClO$_4$ | 7 | 2.507 ± 0.100 | 0.1 | 2.197 ± 0.099 | 0.1 | .326 ± 0.029 | .06 |

The values above were calculated for differences between control and experimental groups, using the paired T test. This experiment showed that homocysteine thiolactone perchlorate affected the growth of a malignant neoplasm by causing increased necrosis within the tumor.

EXAMPLE 4

Intensity and Distribution of Arteriosclerotic Lesions from Feeding Homocysteine Derivatives in Synthetic Diet

TABLE 5

Intensity of Arteriosclerotic Lesions from Feeding Homocysteine Derivatives in Synthetic Diet

| Compound Administered | Dose (mg/kg/day) | Weeks on Diet | No. of Rabbits | Intensity of Lesions, Aorta Only | P | Intensity of Lesions, Aorta Plus Branches | P |
|---|---|---|---|---|---|---|---|
| — | — | 12 | 6 | 1.7 ± 0.6 | — | 3.0 ± 0.8 | — |
| HCT . HClO$^4$ | 110 | 12 | 6 | 2.5 ± 0.2 | 0.1 | 7.5 ± 1.1 | 0.05 |
| Methionine . HCl | 110 | 12 | 7 | 2.7 ± 0.2 | 0.1 | 8.2 ± 0.8 | 0.01 |
| Homocystine, oxidized with H$_2$O$_2$ | 40–160 | 12 | 8 | 3.0 ± 0.4 | 0.05 | 6.5 ± 0.7 | 0.01 |

2–2.5 kg male New Zealand white rabbits were fed a synthetic diet containing homocysteine thiolactone perchlorate (HCT.HClO$_4$), methionine hydrochloride or oxidized homocystine. The dose of homocystine, oxidized with H$_2$O$_2$, was 40 mg/kg/day for 4 weeks, 80 for 4 weeks, and 160 for 4 weeks. Intensity of arteriosclerosis was assessed semi-quantitatively by assigning arbitrary values to lesions found microscopically. Maximum scores are 4 for aorta and 12 for aorta plus branches. Mean score ± SEM is given for each group. P-values were calculated for differences from control group, using the Student t-test.

TABLE 6

Distribution of Arteriosclerotic Lesions Produced by Homocysteine Derivatives

| Compound Administered | Dose (mg/kg/day) | Weeks | No. of Rabbits | Number of Rabbits with Lesions | | | | |
|---|---|---|---|---|---|---|---|---|
| | | | | Aorta | Heart | Lung | Kidney | Brain |
| — | — | 8 | 6 | 1/6 | 3/6 | 0/6 | 1/6 | 0/6 |
| HCT . HCl | 80 | 4–8 | 6 | 6/6 | 6/6 | 6/6 | 4/6 | 3/6 |
| Methionine | 80 | 4–8 | 6 | 6/6 | 5/6 | 3/6 | 4/6 | 0/6 |
| HCT . HCl | 30 | 8 | 7 | 7/7 | 5/7 | 6/7 | 6/7 | 0/7 |
| HCT . HCl + B6 | 80 | 8 | 3 | 3/3 | 2/3 | 2/3 | 2/3 | 2/3 |
| Methionine + B6 | 80 | 8 | 3 | 3/3 | 3/3 | 3/3 | 2/3 | 1/3 |
| Homocysteic acid | 80 | 8 | 3 | 3/3 | 3/3 | 3/3 | 2/3 | 1/3 |
| — | — | 12 | 6 | 4/6 | 2/6 | 2/6 | 1/6 | 0/6 |
| HCT . HClO$_4$ | 110 | 12 | 6 | 6/6 | 6/6 | 5/6 | 5/6 | 2/6 |
| Methinone . HCl | 110 | 12 | 7 | 7/7 | 7/7 | 7/7 | 6/7 | 3/7 |
| Homocystine, oxidized with H$_2$O$_2$ | 40–160 | 12 | 8 | 8/8 | 5/8 | 7/8 | 2/8 | 3/8 |

The number of animals with arteriosclerotic lesions identified microscopically in the aorta and branches within the major organs is given for groups corresponding to Table 4 above. Sulfur amino acids were given parenterally in the first 7 groups and in a synthetic diet in the last 4 groups. Abbreviations: homocysteine thiolactone hydrochloride (HCT.HCl), homocysteine thiolactone perchlorate (HCT.HClO$_4$), and pryridoxine hydrochloride (B6).

The intensity of arteriosclerotic lesions found in the aorta plus arterial branches was greater in the groups fed the sulfur amino acids, compared to the control group.

I claim:

1. A method of promoting the growth of malignant tumors in laboratory animals such as mice and rabbits which comprises utilizing intraperitoneally an effective amount of homocysteine thiolactone perchlorate in said laboratory animals.

* * * * *